(12) United States Patent
Ragab et al.

(10) Patent No.: US 8,496,706 B2
(45) Date of Patent: Jul. 30, 2013

(54) BONE CAGE WITH COMPONENTS FOR CONTROLLED EXPANSION

(76) Inventors: Ashraf A. Ragab, Brandon, MS (US); James A. Rinner, Franksville, WI (US)

( * ) Notice: Subject to any disclaimer, the term of this patent is extended or adjusted under 35 U.S.C. 154(b) by 29 days.

(21) Appl. No.: 12/848,797

(22) Filed: Aug. 2, 2010

(65) Prior Publication Data
US 2012/0029636 A1    Feb. 2, 2012

(51) Int. Cl.
*A61F 2/44*    (2006.01)
(52) U.S. Cl.
USPC ...................................... 623/17.11
(58) Field of Classification Search
USPC .................. 606/246–249; 623/17.11–17.16
See application file for complete search history.

(56) References Cited

U.S. PATENT DOCUMENTS

| | | | |
|---|---|---|---|
| 5,554,191 A * | 9/1996 | Lahille et al. | 623/17.11 |
| 6,190,414 B1 * | 2/2001 | Young et al. | 623/17.15 |
| 6,454,807 B1 * | 9/2002 | Jackson | 623/17.15 |
| 6,500,205 B1 | 12/2002 | Michelson | |
| 6,569,201 B2 | 5/2003 | Moumene et al. | |
| 6,685,742 B1 * | 2/2004 | Jackson | 623/17.11 |
| 6,743,255 B2 | 6/2004 | Ferree | |
| 6,793,679 B2 | 9/2004 | Michelson | |
| 6,849,093 B2 | 2/2005 | Michelson | |
| 6,852,129 B2 | 2/2005 | Gerbec et al. | |
| 6,962,606 B2 | 11/2005 | Michelson | |
| 6,979,353 B2 | 12/2005 | Bresina | |
| 7,094,257 B2 | 8/2006 | Mujwid et al. | |
| 7,300,465 B2 | 11/2007 | Paul et al. | |
| 7,431,735 B2 * | 10/2008 | Liu et al. | 623/17.11 |
| 7,445,636 B2 * | 11/2008 | Michelson | 623/17.15 |
| 7,828,848 B2 * | 11/2010 | Chauvin et al. | 623/17.16 |
| 8,100,972 B1 * | 1/2012 | Bruffey et al. | 623/17.11 |
| 2001/0034553 A1 | 10/2001 | Michelson | |
| 2002/0072801 A1 | 6/2002 | Michelson | |
| 2002/0128716 A1 * | 9/2002 | Cohen et al. | 623/17.15 |
| 2002/0138146 A1 * | 9/2002 | Jackson | 623/17.15 |
| 2002/0177897 A1 | 11/2002 | Michelson | |
| 2003/0050701 A1 | 3/2003 | Michelson | |
| 2003/0100949 A1 * | 5/2003 | Michelson | 623/17.11 |
| 2003/0208270 A9 | 11/2003 | Michelson | |
| 2004/0087947 A1 * | 5/2004 | Lim et al. | 606/61 |
| 2004/0093084 A1 | 5/2004 | Michelson | |
| 2005/0010294 A1 | 1/2005 | Michelson | |
| 2005/0273173 A1 * | 12/2005 | Gordon et al. | 623/17.16 |
| 2005/0278026 A1 * | 12/2005 | Gordon et al. | 623/17.11 |
| 2006/0058878 A1 * | 3/2006 | Michelson | 623/17.11 |
| 2006/0079962 A1 | 4/2006 | Michelson | |
| 2007/0032871 A1 | 2/2007 | Michelson | |

(Continued)

OTHER PUBLICATIONS

Globus Medical, intervertebral products, http://www.globusmedical.com/products/intervertebral.php.
Stryker, interbody/vertebral body replacement products, http://www.stryker.com/en-us/products/Spine/InterbodyVertebralBodyReplacement/index.htm.

(Continued)

*Primary Examiner* — Eduardo C Robert
*Assistant Examiner* — Michelle C Eckman

(57) ABSTRACT

The present invention is an expandable and adjustable bone cage designed to be used in conjunction with a pedicle screw or plating fusion system. The expandable and adjustable bone cage provides structure for the placement of bone graft material between two adjacent vertebral bodies in order to stabilize or fuse the spine in a predetermined position. The expandable and adjustable bone cage is contoured for easy insertion between vertebral bodies and may be expanded after insertion to maintain, establish or increase lordosis, as well as help secure the bone cage.

21 Claims, 10 Drawing Sheets

U.S. PATENT DOCUMENTS

| | | | |
|---|---|---|---|
| 2007/0282448 A1 | 12/2007 | Abdou | |
| 2008/0021559 A1 | 1/2008 | Thramann | |
| 2008/0046090 A1 | 2/2008 | Paul et al. | |
| 2009/0198339 A1* | 8/2009 | Kleiner et al. | 623/17.16 |
| 2009/0270991 A1 | 10/2009 | Michelson | |
| 2010/0049324 A1* | 2/2010 | Valdevit et al. | 623/17.16 |
| 2010/0057208 A1 | 3/2010 | Dryer et al. | |
| 2010/0168862 A1* | 7/2010 | Edie et al. | 623/17.16 |
| 2011/0130835 A1* | 6/2011 | Ashley et al. | 623/17.11 |

OTHER PUBLICATIONS

Styrker, O.I.C., http://www.europe.stryker.com/index/st_pag_medic-home/st_pag_detailed-product-info/st_pag_spinal-implants/st_pag_detailed-product-info/st_pag_spinal-implants/.

Medtronic, Infuse Bone Graft and the LT-Cage Device, http://www.medtronic.com/your-health/lumbar-degenerative-disc-disease/surgery/our-spinal-fusion-product/infuse/index.htm.

* cited by examiner

BONE CAGE WITH COMPONENTS FOR CONTROLLED EXPANSION

FIELD OF INVENTION

The present invention relates to the field of implants and more particularly to an expandable and adjustable bone cage with a rotatable cam lift for spinal fusions.

GLOSSARY

Figure 1:
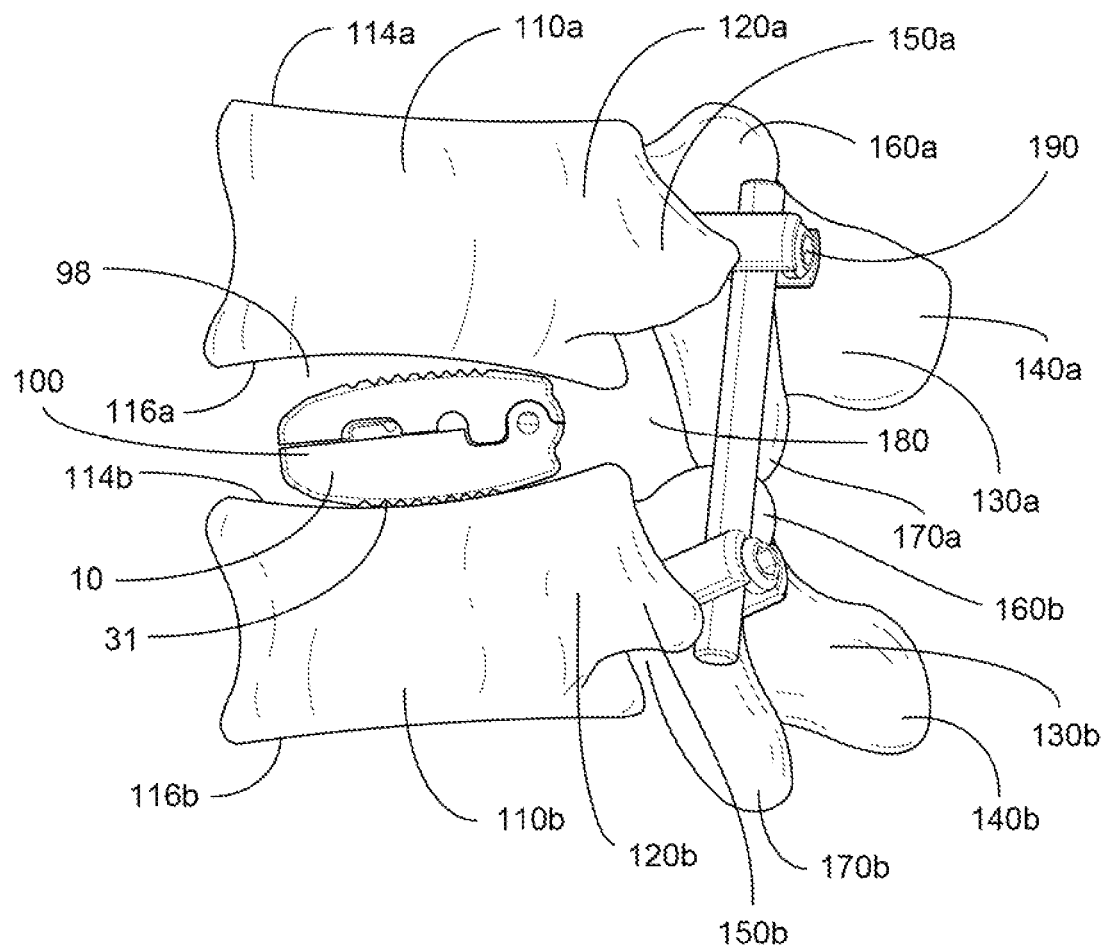
FIG. 1 illustrates a left side view of an exemplary embodiment of an expandable and adjustable bone cage implanted and in a closed/first position.

As used herein, the term "bone cage" refers to an implant that is inserted into the space between vertebrae bodies replacing a damaged vertebra disc and restoring the spacing between the vertebrae.

As used herein, the term "bone graft material" refers to the substance placed in a bone cage that facilitates the growth of new bone tissue. Bone graft material may be artificial (e.g., created from ceramics), synthetic (e.g., made from hydroxylapatite or calcium carbonate), or a natural substance (e.g., bone harvested from another bone in the patient's body (autograft), bone taken from a donor (allograft), or bone morphogenetic proteins (BMPs).

As used herein, the term "cam lift" refers to a component with a rotational driving surface used to expand a bone cage. A cam lift may further serve a safety and control function. For example, a cam lift may be structurally designed to allow only a certain amount of expansion (e.g., 1 mm to 2 mm) to prevent over rotation.

As used herein, the term "cam lift shaft" refers to the circular portion of a cam lift that is placed between the bearing surfaces of the upper and lower bodies of a bone cage.

As used herein, the term "driver" refers to an instrument used to rotate a cam lift.

As used herein, the term "flat spring groove" refers to a channel cut into the side of lower and upper body members that forms a spring tab and allows it to flex.

As used herein, the term "end plug" refers to a component that prevents leakage of bone graft material.

As used herein, the term "lordosis" means inward curvature of the spine.

As used herein, the term "pivotally attached" means two or more components connected at a pivot point.

As used herein, the term "pivot mechanism" refers to an assembly of two or more moving parts that turn or rotate upon each other.

As used herein, the term "pivot retention catch" refers to a component that protrudes from a first body member of a bone cage and latches into a corresponding pivot retention hole in a second body member of the bone cage.

As used herein, the term "pivot retention hole" refers to an aperture in a body member of a bone cage that is adapted to receive a pivot retention catch.

As used herein, the term "pivot surface" refers to the concave and convex portions of the first body member that fit against the convex and concave portions of the second body member of a bone cage. When the bone cage is expanded, the pivot surfaces of the first body member rotate along the pivot surfaces of the second body member.

As used herein, the term "positional flats" refers to a series of flattened segments that encircle a portion of a cam lift. When the cam lift is rotated, the positional flats press against the spring tab of the lower and upper body members of a bone cage.

As used herein, the term "spring tab" refers to a portion of the lower and upper body members of a bone cage that flexes during rotation of the cam lift and returns to position when the final position of the cam lift is reached.

As used herein, the term "surface engaging contour" refers to a portion of a lower or upper body member shaped to mate with the other body member.

As used herein, the term "vertebral engaging contour" refers to a portion of a lower or upper body member that is shaped to better conform to a part of a vertebral body endplate.

BACKGROUND

Spinal fusion surgery for degenerative disc disease involves removing the damaged disc and replacing it with bone grafted from another site on the patient's body, bone from a donor, or artificial or synthetic bone graft material that stimulates bone growth to fuse, or join, the two vertebrae together to stabilize the spine. In all spinal interbody fusion surgeries, disc material is removed. A spacer, referred to as a "cage" is then inserted into the disc space.

The fusion cages help separate the vertebral bodies, taking pressure off the spinal nerves, which travel from the spinal canal through openings, each called the neural foramen. The expansion pulls the ligaments inside the spinal canal taut so they don't buckle into the spinal canal and cause compression of the nerves. Surgeons monitor the position and correct placement of the cages using fluoroscopy and Electromyography (EMG) monitoring.

Fusion cages known in the art are most commonly made of metal, graphite, bone, or PEEK (polyether ether ketone). Many of these cages are shaped like cylinders. A few are rectangular in shape. The main purpose of the cage, regardless of the shape or material, is to hold the two vertebrae apart while the fusion becomes solid.

Generally, two cages are placed side by side within the disc space spreading the vertebrae apart. After implanting the cages, most surgeons attach metal hardware or screws to the vertebrae to rigidly lock them in place. This allows the bone graft to effectively fuse the vertebrae together.

The hollow center of the cage is packed with bone graft material, either in the form of natural bone taken from another site on the patient or from a donor or an artificial or synthetic bone substitute.

When bone is taken from another part of the patient's own body (i.e., autograft), there is a risk of pain, infection, or weakness in the area where the graft is taken. Synthetic bone growth alternatives offer an alternative to using the patient's own bone. Using gene therapy, scientists have produced bone graft substitutes (i.e., growth factors). These growth factors are natural proteins found in the human body. Genetic engineers have been able to clone proteins known as bone morphogenetic proteins (BMPs). These proteins are then made available as powder, small particles, or chips. Hormones that circulate in the bloodstream act on the BMP molecules, causing them to build new bone tissue.

The growth factor that is approved for lumbar fusion with titanium fusion cages is BMP-2. Substituting BMP-2 for an autograft eliminates complications and the recovery associated with harvesting autograft material from the patient's own body. One example of a commercially available bone growth material is Infuse® Bone Graft by Medtronic.

A risk associated with the use of bone growth material is that the nerves may be exposed to the material causing bone formations around or adjacent to the nerves, which can cause severe neurological injury or paralysis.

There are three different approaches for spinal fusion surgeries: anterior, posterior and lateral. Anterior interbody spinal fusion is performed via an incision in the patient's abdomen and the vertebral bodies are approached from the front. This approach is generally used when the surgeon needs to reach the front part of the spine. The abdominal muscles must be displaced resulting in considerable patient discomfort and increased recovery time. The use of bone formation material is currently approved by the FDA only for the anterior approach, because this approach reduces risk of exposing the lumbar nerves to the bone growth material.

Posterior interbody spinal fusion is performed from an incision made in the back. The posterior approach is necessary if a decompression procedure is performed in addition to a spinal fusion. The use of bone formation material poses considerable risk since the lumbar nerves are exposed during the procedure. Any displacement of the bone formation material can cause substantial nerve damage.

Lateral spinal fusion techniques have been gaining popularity. The procedure is performed through the patient's side, avoiding the major muscles of the abdomen and back. With recent advances in neurologic monitoring capabilities, surgeons are able to safely navigate around the lumbar nerves in order to enter the disc space laterally. However, synthetic bone growth material is not currently approved by the FDA for use in lateral spinal fusion procedures.

Each vertebra has a pair of transverse processes, one on each side of the spinal column. Spinal muscles attach to the transverse processes. The pedicle, a short projection of bone, lies between the back of the vertebral body and the transverse process and extends from the spinal column in the back to the vertebral body in front.

Pedicle screws can be used alone or in conjunction with bone cages. Using the "posterior approach," pedicle screws are placed into the pedicles. Each patient's pedicles are of a different size, so the screws are available in different diameters and lengths. Two screws are placed into each vertebra (one in each of two pedicles).

A problem known in the art is that when a disc is removed and pedicle screws are inserted, there is a loss of support due to the displacement of the disc material that is normally in contact with the endplates. Displacement of disc material leaves a void and pressure formerly absorbed by the disc material is partially redistributed to a component held in place with pedicle screws. It is desirable to minimize the amount of force placed on the pedicle screws to avoid breakage of the pedicle screw system. It is further desirable to fill the void left by the removal of disc material in a manner that maximizes contact of the device (e.g., a bone cage known in the art) with the endplates. It is critical that any device placed in the space formerly occupied by the disc has effective contact with the endplates in order for the surgery to promote the fusion of the vertebrae and to avoid fracture of the endplates. This fusion process is the objective of the surgery, and the success of the surgery depends on how effectively fusion occurs.

A bone cage(s) is placed in the disc space while the pedicle screws are in the two pedicles. With the bone cage in place, the pedicle screws are compressed along the rods which will shorten the posterior column, and the bone cage will maintain the anterior column height by keeping the disc space distracted, thereby restoring lordosis of the lumbar spine. The rods are then tightened to the screws to hold the spine in its new position until the bone graft fuses. The bone cage and pedicle screws have stability (the implant in front, and the two screws in back) forming a triangle.

Prior to fusion, and prior to inserting the bone cage, pedicle screws absorb the stress of supporting the spine. In older patients, bone is weaker and the pressure of the pedicle screws can cause osteoporotic complications. Thus, it is desirable, when possible, to effectively balance the pressure placed on the pedicle screws and on the bone cages. This requires that the bone cage make effective contact with the endplate of the two vertebrae bodies during the fusion process.

There are many versions of bone cages known in the art, and many attempts have been made to solve the problem of stable placement of bone cages with the optimum and controlled contact with the vertebral endplates. However, devices known in the art are associated with problems due to incomplete or uncontrolled contact between the endplates of the vertebral bodies and the upper and lower surfaces of the cage. Many attempts have been made in the art to create bone cages which can be adjusted or positioned to account for physiological differences in patients and achieve pressure reduction.

Bone cages, such as the Continental™ and Colonial™ by Globus Medical, have a chamfered leading edge to facilitate insertion in multiple footprints, heights, and profiles allowing the surgeon to match various patient anatomies. However, these devices cannot be adjusted for a particular patient nor can they be expanded to provide physiologic lordosis (i.e., normal curvature of the lumbar spine where the disc space is wider anteriorly).

The Sustain® O by Globus Medical has a tapered leading edge for easier insertion and rounded corners, which allow for rotation (positioning) during insertion, and thus also attempt to give the physician greater control. The Continental™, Colonial™ and Sustain® O, however, are not desirable because they are not ideally contoured to the shape of the vertebral endplates resulting in a minimal area of contact between the cage and the vertebral endplates. In addition, each bone cage has a fixed height, which cannot be adjusted after insertion.

Bone cages contoured to mimic the shape of vertebral endplates are also available. Globus Medical also has bone cages with varying shapes designed to mimic the shape of vertebral endplates. The Sustain® Small has a convex sagittal profile to mimic the shape of vertebral endplates, Sustain® Large has a trapezoidal footprint to mimic the shape of vertebral endplates, and Sustain® Medium has a teardrop footprint to mimic the shape of vertebral endplates, The LT-Cage® Lumbar Tapered Fusion Device by Medtronic is tapered to more closely match the shape of the disc space.

The AVS TL PEEK and AVS PL PEEK Spacer Implants by Stryker are also available in a shape that more closely mimics the shape of the vertebral endplates. Each is available in rectangular or parallel (0 degree) and wedge (4 degree) as well as in varying heights and two different lengths/widths. The Ogival Interbody Cage implant by Stryker is a bullet shaped cage to facilitate intracanal navigation and is available in 4 degree and 8 degree lordotic versions to provide better coverage. In addition, the AVS TL PEEK, AVS PL PEEK, and Ogival Interbody Cage implants include serrations on the top and bottom weight bearing surfaces to provide stability and prevent migration. Each of these bone cages is uniquely shaped and designed to mimic the contours of the vertebral endplates, however, the correct bone cage and the correct size/height must be chosen in order to match each patient's particular anatomy. None of these bone cages are capable of being adjusted to conform to a particular patient's vertebral endplates.

Other types of expandable bone cages, such as the VBoss Implant by Stryker are also expandable, The VBoss Implant has an expandable column with modular end caps that are available in 5 diameters with 0, 5, or 10 degree angles to enhance restoration of lordsis. The XPand® by Globus Medical is an expandable cage that comes in a variety of footprints, heights, and lordotic angles. Both of these devices can be expanded vertically; however, these cages are indicated in cases to replace the whole vertebra body after the entire vertebral bone is removed.

U.S. Pat. No. 6,852,129 (Gerbec '129) teaches a wedge-shaped bone fusion implant with expandable sidewalls that allows the height of the implant to be adjusted when a component is inserted for expansion. This design requires that the physician manually control expansion and determine the position of the plates of the device without mechanical guidance or physical precision. In addition, the flattened and rectangular plates of the device do not accomplish effective contact with the endplates, and this leaves a gap between the surfaces of the device and the endplates.

U.S. Pat. No. 6,962,606 (Michelson '606) teaches an adjustable "push in" implant by which the "front, back or both" of the implants are raised by "the same or various amounts." The implant taught by Michelson '606 is expandable; however, Michelson '606 is not enabling and does not teach one of ordinary skill in the art how to make or use a bone cage.

Several problems are associated with this device. Michelson '606 does not enable a device which effectively makes contact with the endplates of the vertebral bodies because the device is comprised of two flattened (or uniformly curved) panels that do not conform to the contours of the vertebral bodies and thus the objective of the device of reducing pressure on the pedicle screws and equalizing the pressure over the surface of the device is not effectively achieved despite the capability of the device to be expanded in place. More significantly, placement of the Michelson '606 device requires a rectangular "blocker" component to keep the ends apart and the expansion is not effectively controlled. In addition, this device has only two positions: open or closed.

Michelson teaches expanding the implant with an unspecified tool "such as a spreader or distracter [or] scissor type" device. No method for expanding the device is disclosed or claimed, and a "scissor type" device cannot provide adequate control, which is critical during placement of the cage. Michelson '606 does not allow for controlled expansion of the device, which can result in substantial risk to a patient because the bone cage may pack or break through the bone of the vertebral bodies.

The device disclosed in Michelson may potentially be dislodged because it does not have secure points of contact. In addition, the lack of secure points of contact results n an unpredictable reduction of pressure over the pedicle screws.

It is desirable to have a bone cage that allows for maximum control and predictability of expansion, and which protects the endplates from fracture by distributing the forces along a greater surface area.

It is desirable to have a bone cage that is in secure contact with the endplates of the vertebral bodies.

It is desirable to have a modular system that allows the surgeon to size the implant to accommodate patients with varying size disc spaces and/or disc heights.

It is desirable to have a reliable means for expanding a bone cage device.

It is desirable to have a bone cage which reduces pressure on pedicle screws during the fusion process by maximizing contact between the bone cage and the vertebral endplates through the use of anthropometric contours.

It is desirable to have a bone cage which is shaped to conform to the contours of the vertebral endplates and which is capable of expanding at an angle optimum for controlled support and to prevent the device from being displaced while restoring lordosis to the spinal column.

It is further desirable to have a bone cage which is adapted for insertion of bone graft material after the device is stably in place, minimizing the risk that the bone graft material will be displaced or come in contact with the nerves during implantation.

SUMMARY OF THE INVENTION

The present invention is an expandable and adjustable bone cage designed to be used in conjunction with a pedicle screw or plating fusion system. The expandable and adjustable bone cage provides structure for the placement of bone graft material between two adjacent vertebral bodies in order to stabilize or fuse the spine in a predetermined position. The expandable and adjustable bone cage is contoured for easy insertion between vertebral bodies and may be expanded after insertion to maintain, establish or increase lordosis, as well as help secure the bone cage.

The expandable and adjustable bone cage is shaped to the normal concave elliptical endplates of the vertebral bodies, and includes modular components for accommodating differences in disc space size. The bone cage is also designed to expand in steps so that the proper amount of distraction and lordosis can be customized to the individual patient.

DETAILED DESCRIPTION OF INVENTION

For the purpose of promoting an understanding of the present invention, references are made in the text to exemplary embodiments of an expandable and adjustable bone cage, only some of which are described herein. It should be understood that no limitations on the scope of the invention are intended by describing these exemplary embodiments. One of ordinary skill in the art will readily appreciate that alternate but functionally equivalent materials, dimensions and designs may be used. The inclusion of additional elements may be deemed readily apparent and obvious to one of ordinary skill in the art. Specific elements disclosed herein are not to be interpreted as limiting, but rather as a basis for the claims and as a representative basis for teaching one of ordinary skill in the art to employ the present invention.

It should be understood that the drawings are not necessarily to scale; instead, emphasis has been placed upon illustrating the principles of the invention. In addition, in the embodiments depicted herein, like reference numerals in the various drawings refer to identical or near identical structural elements.

Moreover, the terms "substantially" or "approximately" as used herein may be applied to modify any quantitative representation that could permissibly vary without resulting in a change in the basic function to which it is related.

FIG. 1 illustrates a left side view of an exemplary embodiment expandable and adjustable bone cage 100 implanted and in a closed/first position. Shown in FIG. 1 are two vertebra comprised of vertebral bodies 110a, 110b, pedicles 120a, 120b, lamina 130a, 130b, spinous processes 140a, 140b, transverse processes 150a, 150b, superior articular facets 160a, 160b, inferior articular facets 170a, 170b, and spinal canal 180. Also visible is pedicle screw fusion system 190.

Vertebral bodies 110a, 110b are the main portion of vertebra and bear about 80% of the body's weight while standing. Between vertebral bodies 110a 110b is disc space 98, where an intervertebral disc (not shown) is normally located. Each vertebral body 110a, 110b has top endplate 114a, 114b and bottom endplate 116a, 116b, which provide an attachment for the intervertebral disc.

Pedicles 120a, 120b are cylinder-shaped projections of hard bone that stick out from the back part of vertebral bodies 110a, 110b. Pedicles 120a, 120b serve as pillars, joining the front and back parts of the vertebra, and provide side protection for the spinal cord and nerves.

Lamina 130a, 130b serve as the roof of spinal canal 180 providing support and protection for the backside of the spinal cord. Spinous processes 140a, 140b are bony projections that arise at a right angle to the midline of lamina 130a, 130b. Each spinous process 140a, 140b is attached to the spinous process above and below it by ligaments (i.e., spinous process 140a is attached to spinous process 140b).

Transverse processes 150a, 150b are located at right angles to the junction of pedicles 120a, 120b and lamina 130a, 130b. Transverse processes 150a, 150b provide a place for the back muscles to attach to the spine.

Spinal canal 180 is a bony tunnel surrounding the spinal cord. Spinal canal 180 is made up of the front of vertebral body 110a, 110b, pedicles 120a, 120b on the sides of vertebral body 110a, 110b, and lamina 130a, 130b in the back. In the lower back, spinal canal 180 also contains the nerve roots of the lower spine.

Mating superior articular facets 160a, 160b and inferior articular facets 170a, 170b connect each vertebra to the vertebrae above and below it.

In the embodiment shown, the intervertebral disc has been removed and bone cage 100 has been implanted into disc space 98 between vertebral body 110a and vertebral body 110b. Bone cage 100 is inserted posteriorly. The shape of bone cage 100 allows it to be inserted flat into disc space 98 without the need to distract vertebral bodies 110a, 110b, minimizing retraction of the nerve root and the resulting injury and scarring.

In the embodiment shown, bone cage 100 is in the closed/first position and outer surface 31 of lower body 10 of bone cage 100 rests against top endplate 114b of vertebral body 110b.

Figure 2:
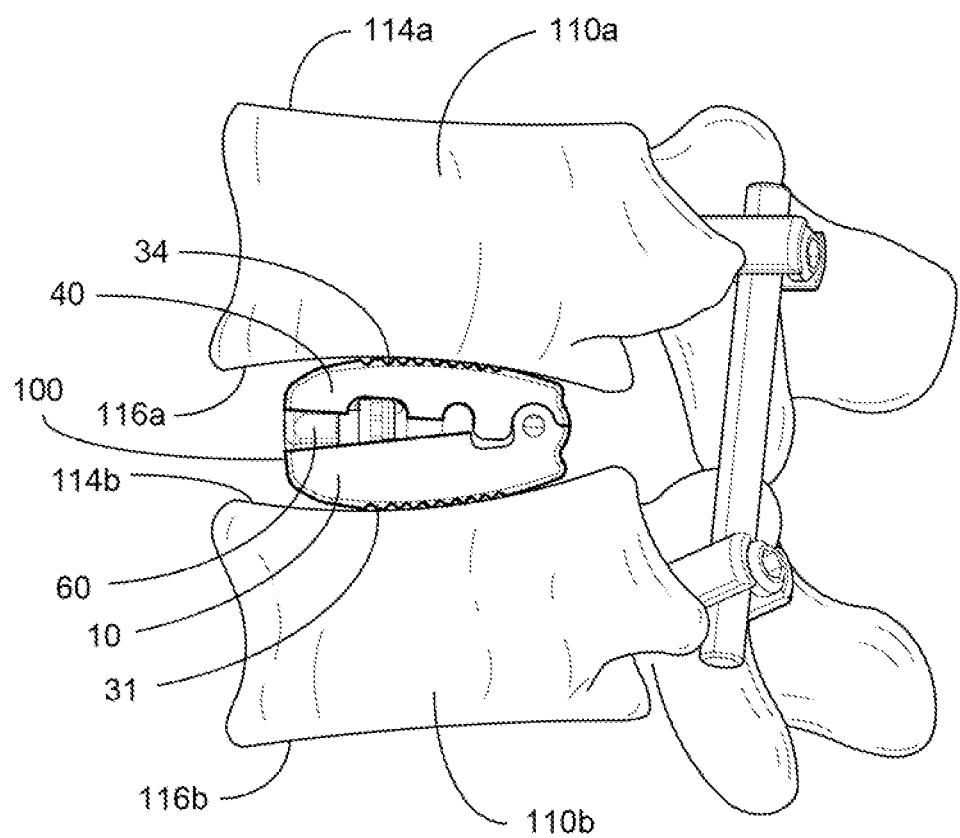
FIG. 2 illustrates a left side view of an exemplary embodiment of an expandable and adjustable bone cage implanted and in an expanded position.

FIG. 2 illustrates a left side view of an exemplary embodiment of expandable and adjustable bone cage 100 implanted and in an expanded position. After bone cage 100 has been implanted, it can be pivotally expanded by rotating cam lift 60 to provide for maximum surface contact between expandable and adjustable bone cage 100 and vertebral bodies 110a, 110b. In the embodiment shown, cam lift 60 is accessible through the distal end of bone cage 100 between lower body 10 and upper body 40.

Outer surfaces 31, 34 of bone cage 100 are convexly-shaped to conform to the concave shape of endplates 114b, 116a of vertebral bodies 110a, 110b. In the embodiment shown, bone cage 100 is expanded until outer surface 34 of upper body 40 rests against bottom endplate 116a of vertebral body 110a.

Expanding bone cage 100 increases the amount of contact between outer surface 34 of upper body 40 and bottom endplate 116a of vertebral body 110a, promoting healing and fusion by distributing the weight and pressure of vertebral bodies 110a, 110b more evenly over the length of bone cage 100 allowing restoration of lordosis with compression of the pedicle screw fusion system 190. In addition, distributing the weight of vertebral bodies 110a, 110b onto bone cage 100 decreases the amount of stress placed on pedicle screw fusion system 190 and the likelihood that screws will loosen, further delaying healing.

Figure 3:
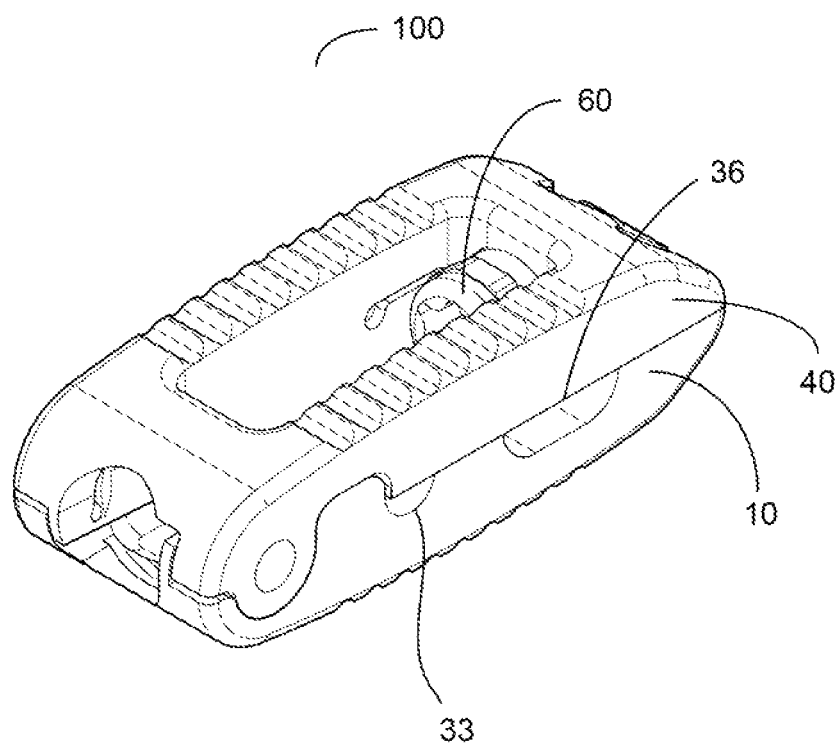
FIG. 3 illustrates a perspective view of the proximal end of an exemplary embodiment of an expandable and adjustable bone cage in a closed/first position.

FIG. 3 illustrates a perspective view of the proximal end of an exemplary embodiment of expandable and adjustable bone cage 100 in a closed/first position. In the embodiment shown, bone cage 100 is comprised of lower body 10, upper body 40, cam lift 60. Bone cage 100 may be expanded by rotating cam lift 60.

In an exemplary embodiment, lower body 10 and upper body 40 are identical, reducing the cost and time of manufacturing. In various embodiments, lower body 10 and upper body 40 are available in varying heights. In the embodiment shown, bone cage 100 is assembled using lower body 10 and upper body 40 of identical heights (e.g., 4 millimeters); however, in other embodiments, bone cage 100 may be assembled using lower body 10 and upper body 40 having varying heights (e.g., 4 millimeter lower body and 5 millimeter upper body) to accommodate differences in the distance between vertebral bodies in patients. Inner surface 33 of lower body 10 mates with inner surface 36 of upper body 40. Mating inner surfaces 33 and 36 allow lower body 10 and upper body 40 to fit together even when a lower body and upper body of different heights are used.

Lower body 10 and upper body 40 are selected based on the desired height. Once selected, cam lift 60 is placed between lower body 10 and upper body 40 and lower body 10 and upper body 40 are snapped together.

In the embodiment shown, bone cage 100 has a length of approximately 25 to 30 millimeters, a height of approximately 6 to 7 millimeters in the closed/first position. In the embodiment shown, bone cage 100 is capable of expanding 2 to 3 millimeters; however, in other embodiments, may be capable of expanding more than 3 millimeters.

In the embodiment shown, bone cage 100 is comprised of titanium; however in other embodiments, may be comprised of another material including, but not limited to PEEK, tricalcium phosphate, ceramics, metallic alloys, or any other implantable material.

Figure 4:
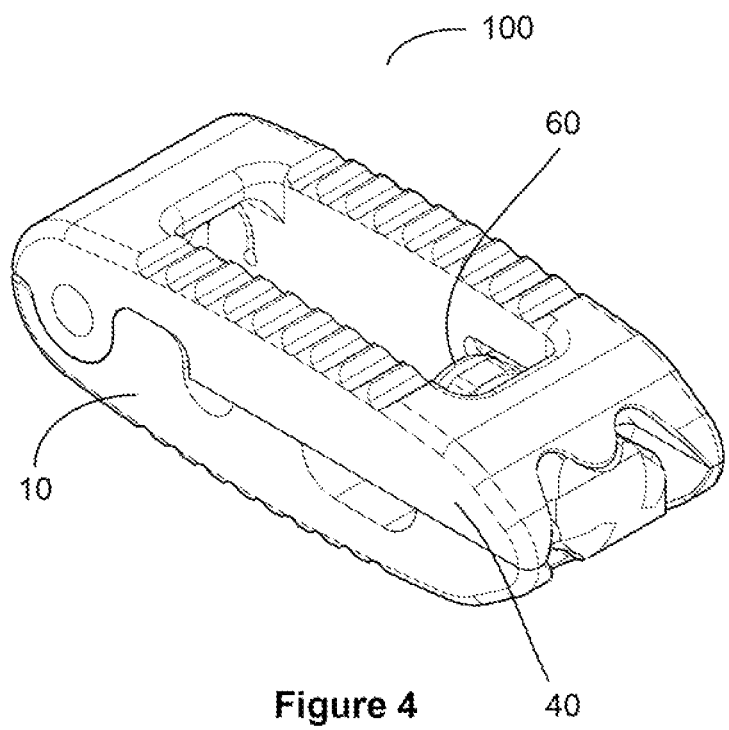
FIG. 4 illustrates a perspective view of the distal end of an exemplary embodiment of an expandable and adjustable bone cage in a closed/first position.

FIG. 4 illustrates a perspective view of the distal end of an exemplary embodiment of expandable and adjustable bone cage 100 in a closed/first position. In the embodiment shown, bone cage 100 is comprised of lower body 10, upper body 40, and cam lift 60.

Figure 5A:
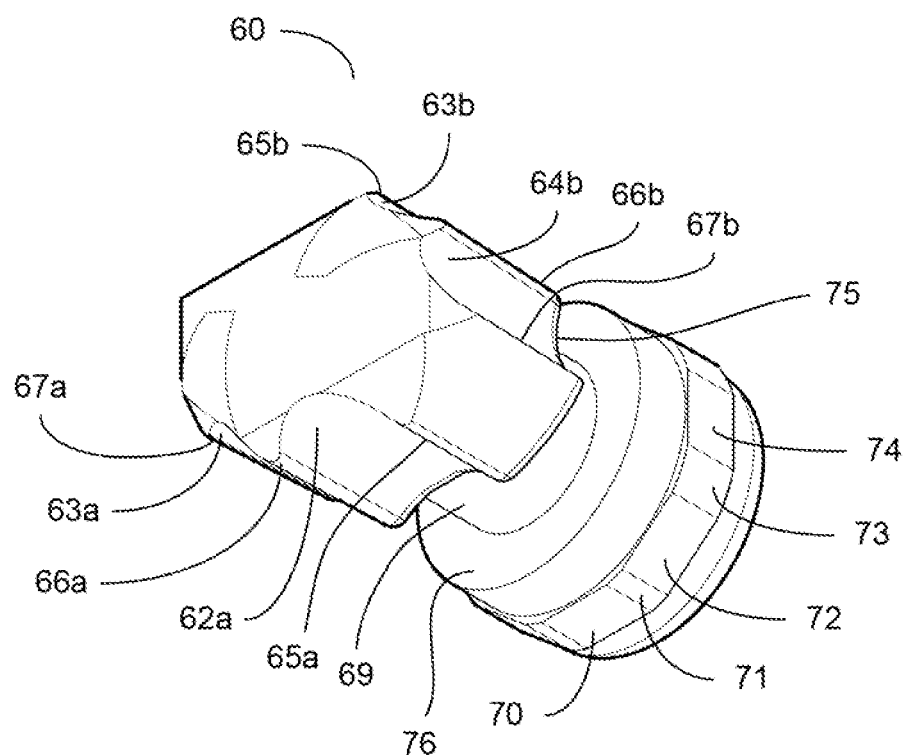
FIG. 5a illustrates a perspective view of an exemplary embodiment of a cam lift for an expandable and adjustable bone cage.

FIG. 5a illustrates a perspective view of an exemplary embodiment of cam lift 60. Cam lift 60 includes a plurality of nesting surfaces 62a, 62b, 63a, 63b, 64a, 64b and cam lift lobes 65a, 65b, 66a, 66b, 67a, 67b, When cam lift 60 is in a closed/first position, nesting surfaces 62a, 62b mate with cam lift followers 45, 15 (not shown) of upper body 40 and lower body 10 (not shown, see FIG. 8c). To expand expandable and adjustable bone cage 100 to a first expanded position, cam lift 60 is rotated one step so that nesting surfaces 63a, 63b mate with cam lift followers 45, 15 of upper body 40 and lower body 10 (see FIG. 12). Nesting surfaces 64a, 64b mate with cam lift followers 45, 15 (see FIG. 15) when cam lift 60 is rotated to a second expanded position. In other embodiments, cam lift 60 may have more or fewer cam lift lobes and/or nesting surfaces.

Figure 6:
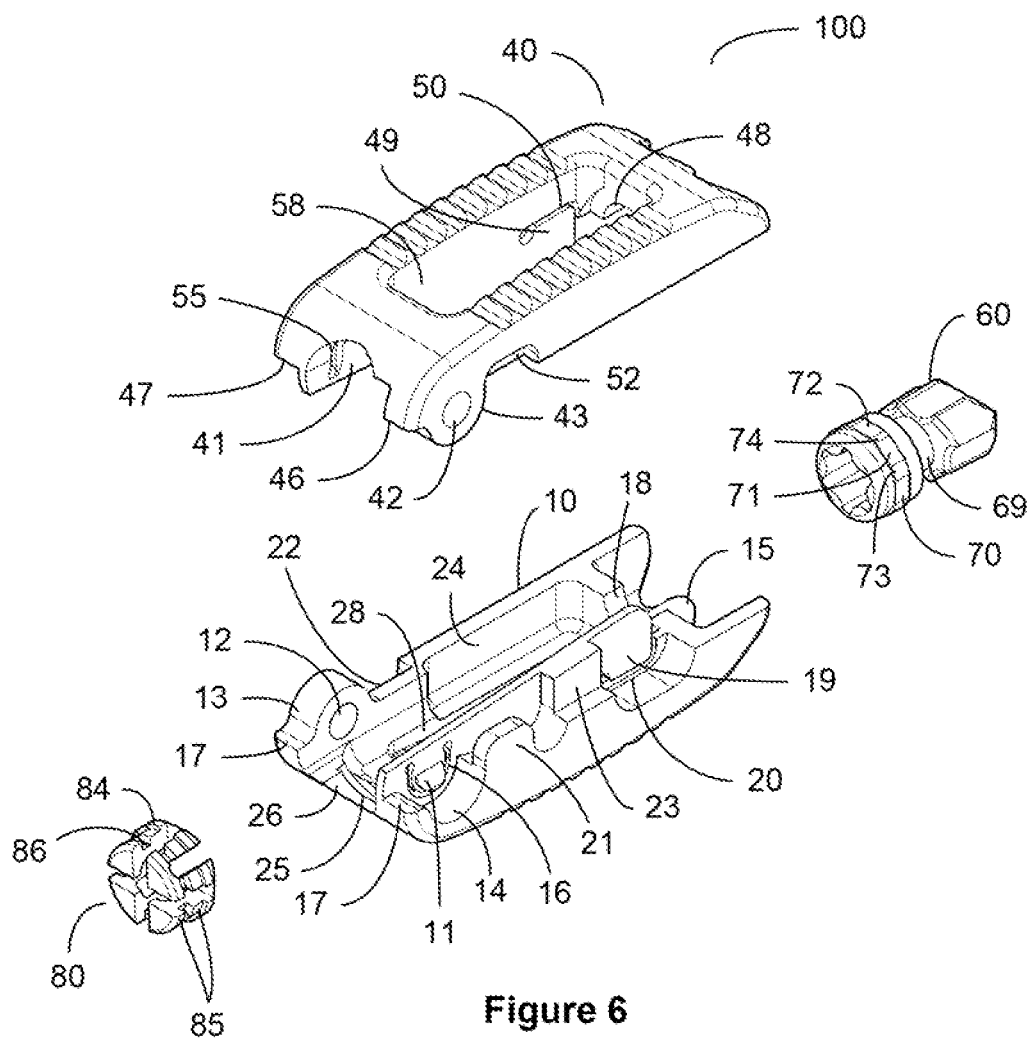
FIG. 6 illustrates an exploded view of the proximal end of an exemplary embodiment of an expandable and adjustable bone cage.

Also visible is cam shaft 69 which rests between bearing surfaces 48 of upper body 40 (not shown) and bearing surface 18 (not shown) of lower body 10 (not shown) (see FIG. 6).

In the embodiment shown, cam lift 60 further includes a plurality of positional flats, e.g., 70, 71, 72, 73, 74, around the proximal end. The function of the positional flats is to prevent accidental rotation of the cam lift giving the surgeon added control when placing and expanding bone cage 100. Positional flats are designed to engage spring tab 49 of upper body 40 (not shown) and spring tab 19 of lower body 10 (not shown) (see FIG. 6).

Figure 5B:
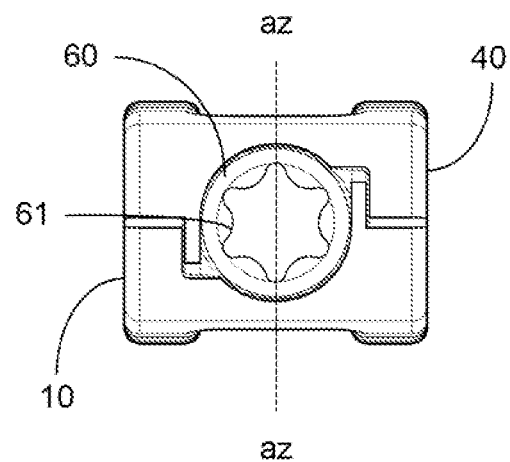
FIG. 5b illustrates a proximal view of an exemplary embodiment of an expandable and adjustable bone cage in a closed/first position.

FIG. 5b illustrates a proximal view of an exemplary embodiment of expandable and adjustable bone cage 100. Cam lift 60 and cam lift rotational driving surface 61 are accessible through the proximal end of bone cage 100 between lower body 10 and upper body 40.

In the embodiment shown, cam lift rotational driving surface 61 has a hexalobe design with six driving slots that correspond to and are adapted to receive a hexalobe driver. However, in other embodiments, cam lift rotational driving surface 61 can be any polygon or another shape and may have any number or style of driving slots to correspond to a particular style of driver.

In the embodiment shown, the plane represented by line az is fixed on the vertical center of cam lift 60 when it is in the first position, that is, when bone cage 100 is closed.

FIG. 6 illustrates an exploded view of the proximal end of exemplary embodiment of an expandable and adjustable bone cage 100 showing lower body 10, upper body 40, cam lift 60, and optional end plug 80.

Prior to assembly, lower body 10 and upper body 40 are selected based on height and cam lift 60 is placed in its first position, that is, so that nesting surfaces 62a, 62b rest against cam lift followers 15, 45 (not visible). Cam lift shaft 69 is placed between cam lift bearing surface 48 of upper body 40 and cam lift bearing surface 18 of lower body 10.

In the embodiment shown, cam lift 60 further includes a plurality of positional flats, e.g., 70, 71, 72, 73, 74, around the proximal end. Positional flats of cam lift 60, e.g., 70, 71, 72, 73, 74, mate with spring tab 49 of upper body 40 and spring tab 19 of lower body 10. Spring tabs 19, 49 are made by adding flat spring grooves 20 (lower body 10), 50 (upper body 60) around the intended spring area. The combination of positional flats and spring tabs help retain cam lift 60 while expandable and adjustable bone cage 100 is in the closed/first, second, and third positions. When cam lift 60 is rotated between first positional flat 73 and second positional flat 74, first positional flat 73 pushes on spring tabs 19, 49 which flex, then return when the final position is reached.

Also shown are pivot surfaces 13, 14, pivot retention catch 11, and pivot retention hole 12 of lower body 10, and pivot surfaces 43, 44 (not visible), pivot retention catch 41, and pivot retention hole 42 of upper body 40. Pivot retention catches 11, 41 are designed to be flexible by pivot retention catch spring grooves 16, 46 and when cam lift 60 is placed in its first position, upper body 40 is snapped into position.

To keep the retention features from sliding apart, tab 21 of lower body 10 mates into recess 52 of upper body 40 and tab 51 (not visible, see FIG. 7a) of upper body 40 mates into recess 22 of lower body 10.

To ensure that spring tabs 19, 49 keep pressure against positional flats 70, 71, and 72 of cam lift 60, outer backing surface 23 of lower body 10 contacts inner backing surface 54 (not visible, see FIG. 7b) of upper body 40 and inner backing surface 24 of lower body 10 contacts outer backing surface 53 (not visible, see FIG. 7b) of upper body 40.

Pivot rotation stops 17, 47 at the proximal end of lower body 10 and upper body 40 limit the amount of pivot and prevent lower body 10 and upper body 40 from pivoting open too far and allowing cam lift 60 to fall out. Cam lift 60 also has distal flange surface 75 (FIG. 5a) and proximal flange surface 76 (FIG. 5a) which prevent cam lift 60 from dislocating.

Figure 17:
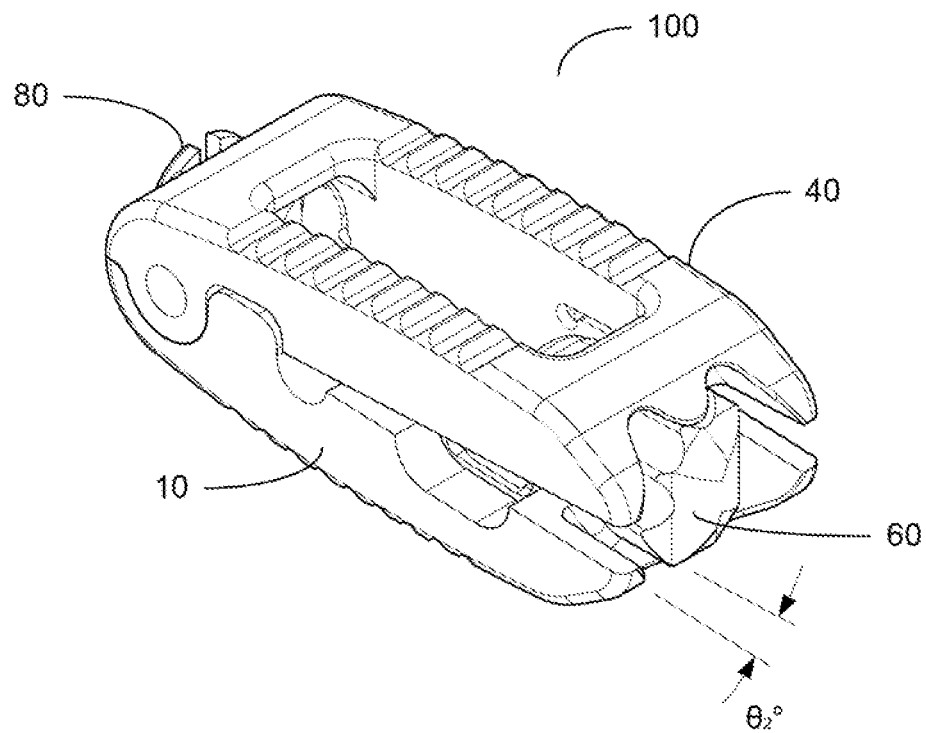
FIG. 17 illustrates a perspective view of the distal end of an exemplary embodiment of an expandable and adjustable bone cage expanded to a third position.

Also shown in FIG. 17 is optional end plug 80. Bone graft material is inserted into bone cage 100 after bone cage 100 is inserted. Optional end plug 80 prevents bone graft material from leaking out of bone cage 100.

In the embodiment shown, optional end plug 80 has a conical nose, radial distal spring slots and radial proximal slots that will allow it to compress when pushed into the proximal end of the upper and lower bodies and expand into graft plug retention grooves 25, 55 of lower body 10 and upper body 40. The tooth configuration that expands while positioned in graft plug retention grooves 25, 55 has perpendicular plug retention shoulder 84 which mates with perpendicular body shoulders (not visible) of lower body 10 and upper body 40 preventing optional end plug 80 from backing out once inserted.

Optional end plug 80 further includes cylindrical plug removal groove 86, which requires a special instrument to compress optional end plug 80 for removal, and an outer cylindrical diameter 85 that mates in the inner cylindrical diameter 26 of lower body 10 and inner cylindrical diameter 56 (not visible) of upper body 40.

In various embodiments, a second cam lift may be used in place of optional end plug 80. After bone cage 100 has been expanded and bone graft material has been inserted, a second cam lift may be inserted into the proximal end of bone cage 100. The second cam lift would allow bone cage 100 to be uniformly expanded.

Figure 7:
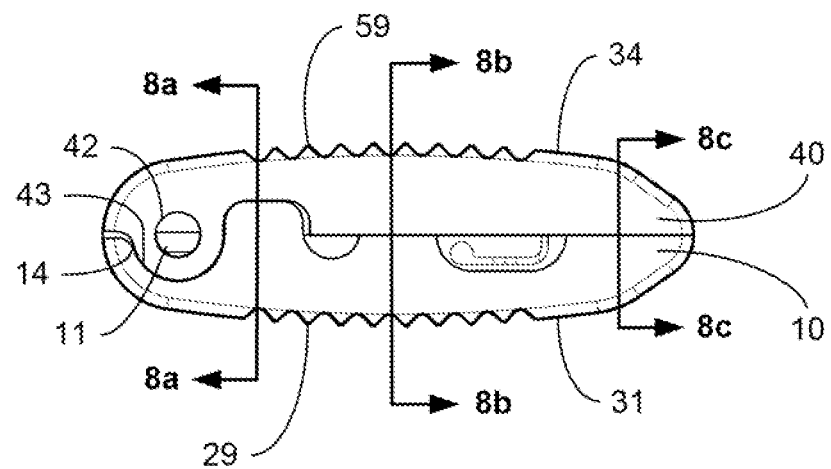
FIG. 7 illustrates a right side view of an exemplary embodiment of an expandable and adjustable bone cage in a closed/first position.

FIG. 7 illustrates a right side view of an exemplary embodiment of expandable and adjustable bone cage 100 in a first/closed position. In the embodiment shown, lower body 10 has pivot surface 14 and pivot retention catch 11, which protrudes from lower body 10, and upper body 40 has pivot surface 43 and pivot retention hole 42.

The left side of bone cage 100 has features identical to that of the right side shown. On the left side of bone cage 100, lower body 10 has pivot retention hole 12 (FIG. 6) and pivot surface 13 (FIG. 6) and upper body 40 has pivot retention catch 41 (FIG. 6) and pivot surface 44 (not visible).

Pivot retention catches 11, 41 secure upper body 40 to lower body 10 and allows pivot surfaces 43, 44 of upper body 40 to pivot into an expanded position along pivot surfaces 13, 14 of lower body 10.

In the embodiment shown, pivot surface 14 of lower body 10 and pivot surface 44 of upper body 40 are concave, and pivot surface 13 of lower body 10 and pivot surface 43 of upper body 40 are convex (see FIG. 6). Pivot surface 14 of lower body 10 fits against pivot surface 43 of upper body 40 and pivot surface 13 of lower body 10 fits against pivot surface 44 of upper body 40 when lower body 10 and upper body 40 are assembled. When bone cage 100 is expanded, upper body pivot surfaces 43, 44 rotate along lower body pivot surfaces 13, 14 and provide a large contact area between lower body 10 and upper body 40 when bone cage 100 is expanded.

Lower body pivot surfaces 13, 14 and upper body pivot surfaces 43, 44 support the load of the vertebral bodies. The weight of the vertebral bodies is not placed on pivot retention catches 11, 41 and pivot retentions holes 12, 42.

In the embodiment shown, the proximal end of lower body 10 and upper body 40 are rounded with a constant slope forming a semicircle when lower body 10 and upper body 40 are connected. The distal end of lower body 10 and upper body 40 are tapered for easy insertion in the disc space. The rounded shape of the proximal end of bone cage 100 strengthens expandable and adjustable bone cage 100 during insertion.

In the embodiment shown, outer surface 31 of lower body 10 and outer surface 34 of upper body 40 further includes surface engaging contours 29, 69 which contact the endplates of the vertebral bodies and prevent migration of bone cage 100 when positioned. Surface engaging contours 29, 59 produce friction between the vertebral endplates and bone cage 100 to keep bone cage 100 from moving.

Figure 8A:
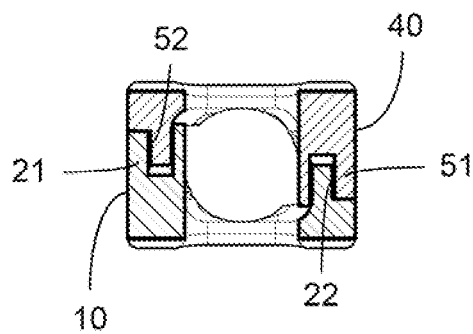
FIG. 8a illustrates a sectional view of an exemplary embodiment of an expandable and adjustable bone cage taken along line 8a of FIG. 7.

FIG. 8a illustrates a sectional view of an exemplary embodiment of expandable and adjustable bone cage 100 taken along line 8a of FIG. 7. In the embodiment shown, lower body 10 has tab 21 and tab recess 22 which correspond to tab recess 52 and tab 51 of upper body 40, respectively. The pairing of tab 21 and recess 52 and tab 51 and recess 22 keep upper body 40 and lower body 10 from separating. In other embodiments, lower body 10 and upper body 40 may have contours, protrusions, or any other corresponding structural configuration which allow lower body 10 and upper body 40 to fit together.

Figure 8B:
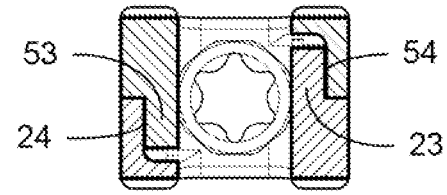
FIG. 8b illustrates a sectional view of an exemplary embodiment of an expandable and adjustable bone cage taken along line 8b of FIG. 7.

FIG. 8b illustrates a sectional view of an exemplary embodiment of expandable and adjustable bone cage 100 taken along line 8b of FIG. 7. In the embodiment shown, lower body 10 has inner backing surface 24 and outer backing surface 23 which correspond to outer backing surface 53 and inner backing surface 54 of upper body 40, respectively.

Figure 8C:
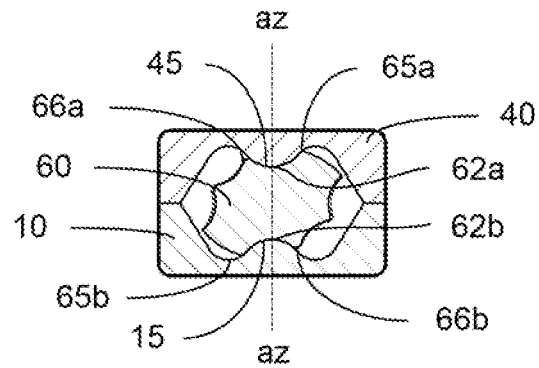
FIG. 8c illustrates a sectional view of an exemplary embodiment of an expandable and adjustable bone cage taken along line 8c of FIG. 7.

FIG. 8c illustrates a sectional view an exemplary embodiment of expandable and adjustable bone cage 100 taken along line 8c of FIG. 7. In the embodiment shown, cam lift 60 is in the closed position and nesting surface 62a (surface between cam lift lobe 65a and cam lift lobe 66a) mates with cam lift follower 45 and nesting surface 62b (surface between cam lift lobe 65b and cam lift lobe 66b) mates with cam lift follower 15.

In the embodiment shown, the plane represented by line az is fixed on the vertical center of cam lift 60 when it is in the first position, that is, bone cage 100 is closed.

Figure 9:
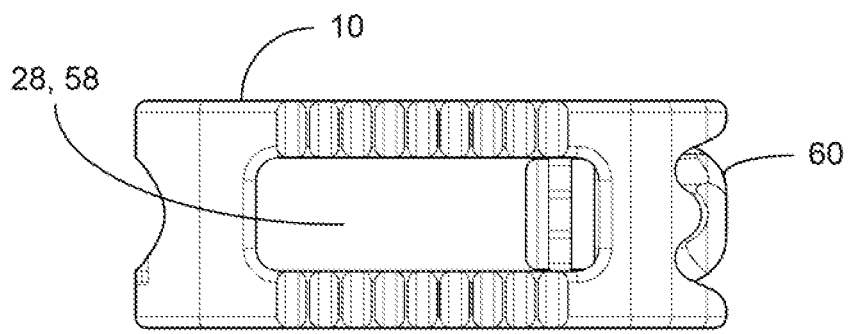
FIG. 9 illustrates a bottom view of an exemplary embodiment of an expandable and adjustable bone cage with a cam lift.

FIG. 9 illustrates a bottom view of an exemplary embodiment of expandable and adjustable bone cage 100 showing cam lift 60 and bone graft openings 28 (lower body 10), 58 (upper body 40) (see FIG. 6).

Figure 10:
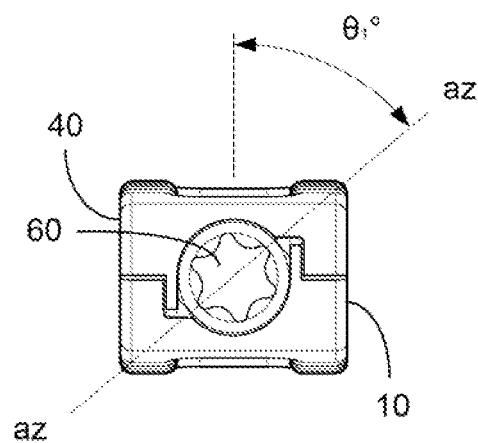
FIG. 10 illustrates a proximal view of an exemplary embodiment of an expandable and adjustable bone cage expanded to a second position.

FIG. 10 illustrates a proximal view of an exemplary embodiment of expandable and adjustable bone cage 100 expanded to a second position. In the embodiment shown, cam lift 60 has been rotated clockwise to a second position raising the distal end of upper body 40. In other embodiments, the lobes on cam lift 60 may be reversed so that the distal end of upper body 40 is raised by rotating cam lift 60 counter-clockwise.

In the embodiment shown, angle $\theta_1$ represents the rotation of plane az and cam lift 60 and the vertical plan through lower body 10 and upper body 40. When cam lift 60 is rotated to angle $\theta_1$, cam lift lobes/nesting surfaces open the distal end of expandable and adjustable bone cage 100.

Figure 11:
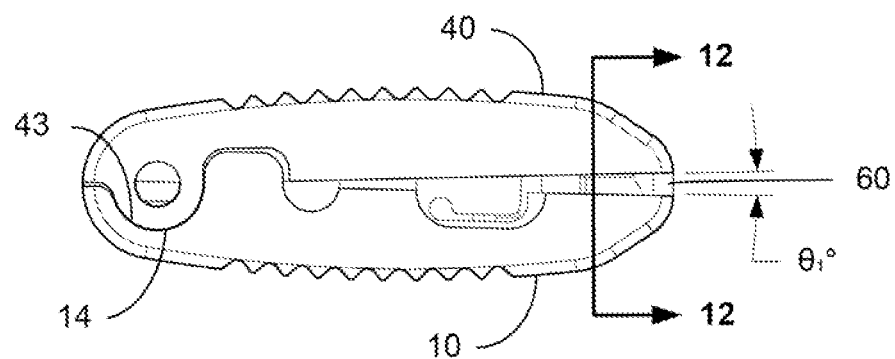
FIG. 11 illustrates a right side view of an exemplary embodiment of an expandable and adjustable bone cage expanded to a second position.

FIG. 11 illustrates a right side view of an exemplary embodiment of expandable and adjustable bone cage 100 expanded to a second position. When cam lift 60 is rotated to a second position, pivot surface 43 of upper body 40 rotates around pivot surface 14 of lower body 10 raising the proximal end of upper body 40.

Figure 12:
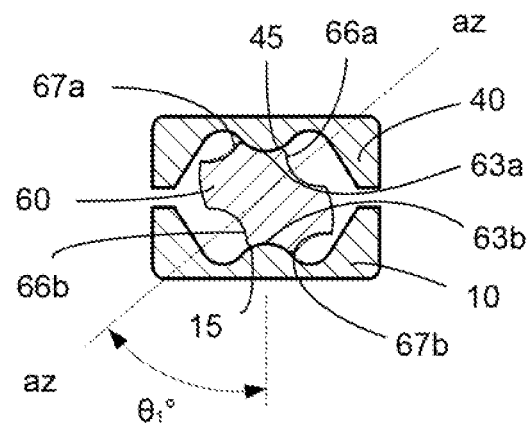
FIG. 12 illustrates a sectional view of an exemplary embodiment of an expandable and adjustable bone cage expanded to a second position taken along line 12 of FIG. 11.

FIG. 12 illustrates a sectional view of an exemplary embodiment of expandable and adjustable bone cage 100 expanded to a second position taken along line 12 of FIG. 11. In the embodiment shown, cam lift 60 has been rotated to a second position so that nesting surface 63a (surface between cam lift lobe 66a and cam lift lobe 67a) mates with cam lift follower 45 and nesting surface 63b (surface between cam lift lobe 66b and cam lift lobe 67b) mates with cam lift follower

15. Nesting surfaces 63a, 63b are machined at angle $\theta_1$ for a mating fit with cam lift followers 45, 15.

When cam lift 60 is rotated clockwise to a second position, cam lift lobes 66a, 66b follow cam lift followers 15 and 45 until nesting surfaces 63a, 63b, mate with cam lift followers 15, 45 securing cam lift 60 into position.

Figure 13:
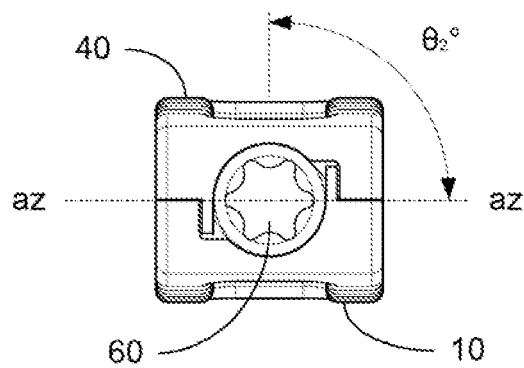
FIG. 13 illustrates a proximal view of an exemplary embodiment of an expandable and adjustable bone cage expanded to a third position.

FIG. 13 illustrates a proximal view of an exemplary embodiment of expandable and adjustable bone cage 100 expanded to a third position. In the embodiment shown, cam lift 60 has been rotated clockwise to a third position raising the distal end of upper body 40. In other embodiments, the lobes on cam lift 60 may be reversed so that the distal end of upper body 40 is raised by rotating cam lift 60 counterclockwise.

In the embodiment shown, angle $\theta_2$ represents the rotation of plane az and cam lift 60 and the vertical plane through lower body 10 and upper body 40. When cam lift 60 is rotated to angle $\theta_2$, cam lift lobes/nesting surfaces open the distal end of expandable and adjustable bone cage 100.

Figure 14:
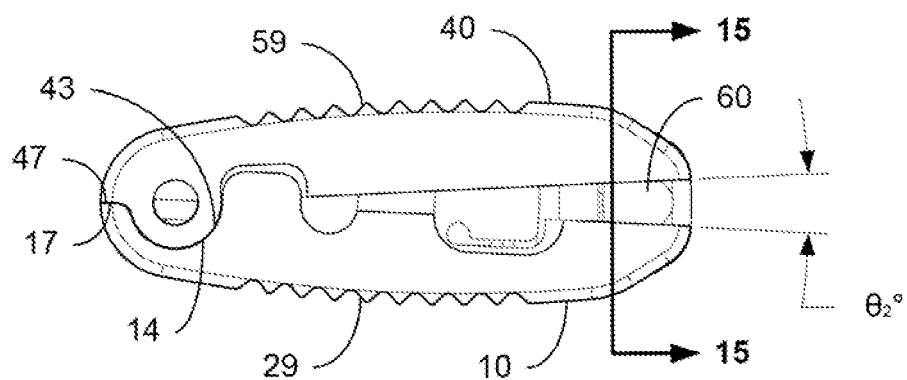
FIG. 14 illustrates a right side view of an exemplary embodiment of an expandable and adjustable bone cage expanded to a third position.

FIG. 14 illustrates a right side view of an exemplary embodiment of expandable and adjustable bone cage 100 expanded to a third position. When cam lift 60 is rotated to a third position, pivot surface 43 of upper body 40 rotates around pivot surface 14 of lower body 10 raising the proximal end of upper body 40.

Also visible are pivot rotation stops 17, 47, which prevent further rotation, and surface engaging contours 29, 59 that contact the endplates of the vertebral bodies when implanted preventing migration of bone cage 100.

Figure 15:
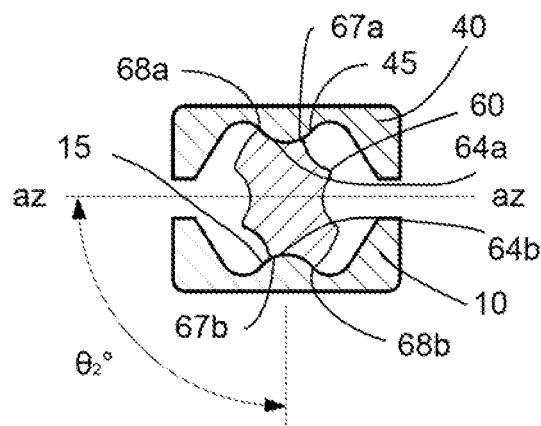
FIG. 15 illustrates a sectional view of an exemplary embodiment of an expandable and adjustable bone cage expanded to a third position taken along line 15 in FIG. 14.

FIG. 15 illustrates a sectional view of an exemplary embodiment of expandable and adjustable bone cage 100 expanded to a third position taken along line 14 in FIG. 13, In the embodiment shown, cam lift 60 has been rotated to a second third position so that nesting surface 64a (surface between cam lift lobe 67a and cam lift edge 68a) mates with cam lift follower 45 and nesting surface 64b (surface between cam lift lobe 67b and cam lift edge 68b) mates with cam lift follower 15. Nesting surfaces 64a, 64b are machined at angle $\theta_2$ for a mating fit with cam lift followers 45, 15.

When cam lift 60 is rotated clockwise to a third position, cam lift lobes 67a, 67b follow cam lift followers 15 and 45 until nesting surfaces 64a, 64b rest against cam lift followers 15, 45 securing cam lift 60 into position. Cam lift edges 68a, 68b are higher and sharper than cam lift lobes 65a, 65b, 66a, 66b, 67a, 67b to help prevent over rotation of cam lift 60.

In the embodiment shown, the shape of cam lift lobes 66a, 66b, 67a, and 67b provides for a smooth transition when cam lift 60 is rotated from a closed/first position to a second (expanded) position or from a second (expanded) position to a third (expanded) position.

Figure 16:
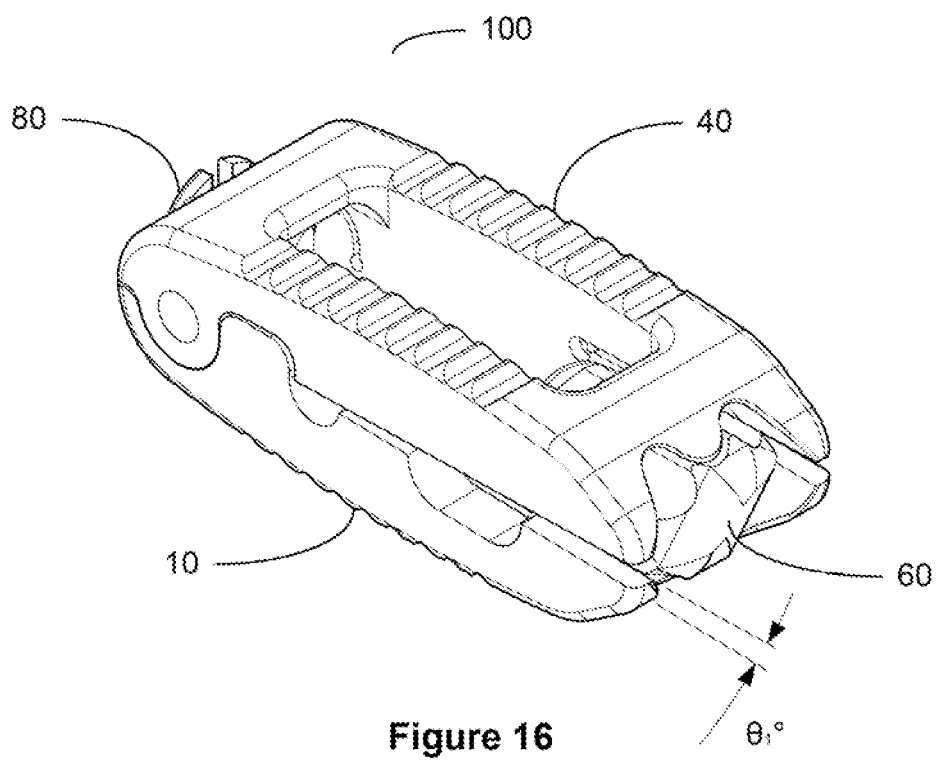
FIG. 16 illustrates a perspective view of the distal end of an exemplary embodiment of an expandable and adjustable bone cage expanded to a second position.

FIG. 16 illustrates a perspective view of the distal end of an exemplary embodiment of expandable and adjustable bone cage 100 expanded to a second position. In the embodiment shown, expandable and adjustable bone cage 100 further includes optional end plug 80.

FIG. 17 illustrates a perspective view of the distal end of an exemplary embodiment of expandable and adjustable bone cage 100 expanded to a third position. In the embodiment shown, expandable and adjustable bone cage 100 further includes optional end plug 80.

Figure 18:
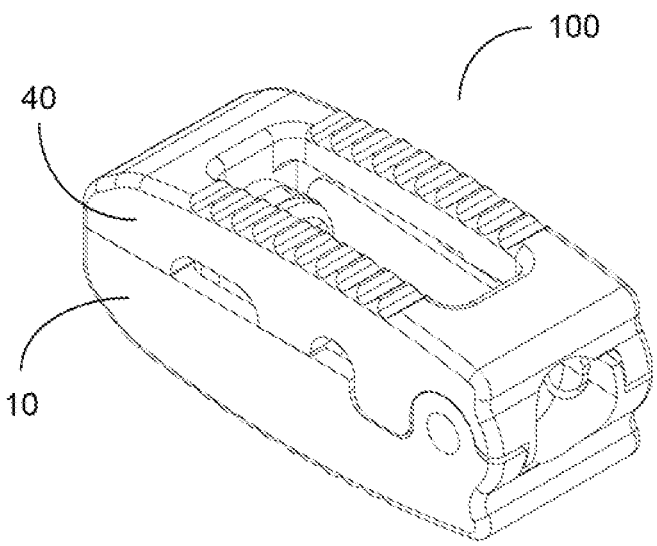
FIG. 18 illustrates a perspective view of the distal end of an exemplary embodiment of an expandable and adjustable bone cage with upper and lower bodies of varying sizes.

FIG. 18 illustrates a perspective view of the distal end of an exemplary embodiment of expandable and adjustable bone cage 100. In the embodiment shown, lower body 10 has a height that is greater than the height of upper body 40. In various embodiments, lower body 10 and upper body 40 may be of the same height or lower body 10 may have a height that is smaller or greater than the height of upper body 40. The height of lower body 10 and upper body 40 selected is determined by the height/size of the patient's disc space.

Figure 19:
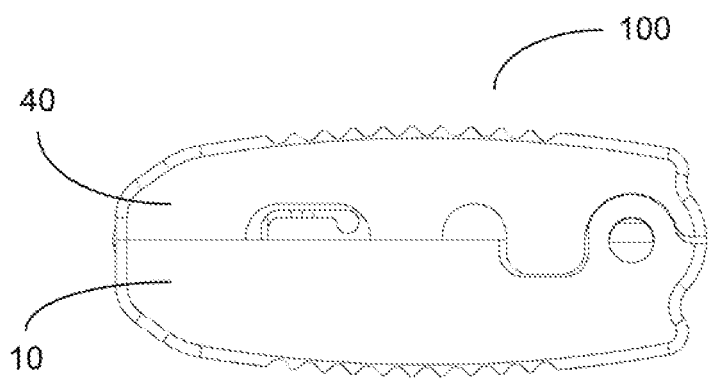
FIG. 19 illustrates a perspective view of the left side of an exemplary embodiment of an expandable and adjustable bone cage with upper and lower bodies of varying sizes.

FIG. 19 illustrates a perspective view of the left side of an exemplary embodiment of expandable and adjustable bone cage 100 with lower body 10 having a height that is greater than the height of upper body 40.

Figure 20:
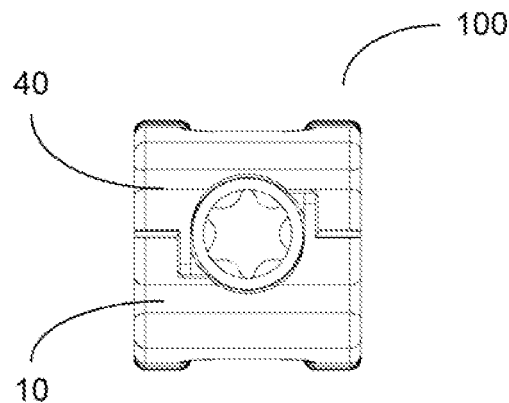
FIG. 20 illustrates a proximal view of an exemplary embodiment of an expandable and adjustable bone cage with upper and lower bodies of varying sizes.

FIG. 20 illustrates a proximal view of an exemplary embodiment of expandable and adjustable bone cage 100 with lower body 10 having a height that is greater than the height of upper body 40.

What is claimed is:

1. A bone cage for controlled expansion comprised of:
   a contoured upper body member of a first selective height comprised of:
      a substantially convexly curved horizontal upper outer surface,
      a mating inner surface,
      a flexible spring tab,
      a contoured cam lift follower,
      at least one bone graft opening, and
      a cam lift bearing surface;
   a contoured lower body member of a second selective height comprised of:
      a substantially convexly curved horizontal lower outer surface,
      a mating inner surface,
      a flexible spring tab,
      a contoured cam lift follower,
      at least one bone graft opening, and
      a cam lift bearing surface;
   wherein said upper body member and said lower body member are discrete components and selectively and pivotally attached to each other at one end;
   wherein said upper body member and said lower body member have tapered distal ends and proximal ends rounded with a constant slope;
   wherein said mating surfaces are in physical contact with each other when in a closed position; and
   at least one cam lift for controlling pivotal movement of the contoured upper body member relative to the contoured lower body member from said closed position to an open position, wherein said cam lift is secured between said contoured upper body member and said contoured lower body member in both said closed position and said open position, said at least one cam lift comprised of:
      a distal end having a plurality of paired cam lift lobes alternated with a plurality of paired nesting surfaces, wherein said nesting surfaces are contoured to mate with said cam followers,
      a proximal end having a plurality of positional flats adapted to engage said spring tabs when said cam lift is rotated, and
      a cam lift shaft in physical rotational contact with said cam lift bearing surfaces.

2. The apparatus of claim 1, which further includes at least one vertebral engaging contour.

3. The apparatus of claim 1, wherein said nesting surfaces mate with a cam lift follower on said upper body member and a cam lift follower on said lower body member.

4. The apparatus of claim 1, wherein said spring tab on said upper body and said spring tab on said lower body comprise a flat spring groove around an intended spring area.

5. The apparatus of claim 1, wherein the said proximal end of said cam lift further includes a rotational driving surface with a plurality of driving slots adapted to receive a driver.

6. The apparatus of claim 5, wherein said rotational driving surface has a hexalobe design with six driving slots.

7. The apparatus of claim 1, which further includes a pivot retention catch and a pivot retention aperture adapted to receive said pivot retention catch.

8. The apparatus of claim 1, wherein said cam lift is accessible through an opening between said upper body member and said lower body member.

9. The apparatus of claim 1, wherein said cam lift can be rotated to expand said apparatus from a closed position to at least one expanded position.

10. The apparatus of claim 1, wherein said first selective height and said second selective height are identical.

11. The apparatus of claim 1, wherein said first selective height and said second selective height are different.

12. The apparatus of claim 1, which has a length ranging from 25 to 30 millimeters.

13. The apparatus of claim 1, wherein said upper body member and said lower body member have a height ranging from 8 to 16 millimeters in the closed position.

14. The apparatus of claim 1, which is capable of expanding 1 or 2 millimeters.

15. The apparatus of claim 1, which further includes an end plug.

16. The apparatus of claim 1, wherein said lower body member and said upper body member further include a plurality of surface engaging contours.

17. A modular bone cage system comprised of:
a plurality of first and second contoured body members of varying heights; wherein the first contoured body member of a first selective height is selectively and pivotally attached to the second contoured body member of a second selective height; is comprised of
a substantially convexly curved horizontal outer surface,
a mating inner surface,
a flexible spring tab,
a contoured cam lift follower,
at least one bone graft opening,
a cam lift bearing surface,
a tapered distal end, and
a proximal end rounded with a constant slope; and
wherein said mating inner surfaces of said first and second contoured body members are in physical contact with each other when in a closed position;
at least one cam lift for controlling pivotal movement of said second body member relative to said first body member, said at least one cam lift comprised of:
a distal end having a plurality of paired cam lift lobes alternated with a plurality of paired nesting surfaces, wherein said nesting surfaces are contoured to mate with said cam followers,
a proximal end having a plurality of positional flats adapted to engage said spring tabs when said cam lift is rotated, and
a cam lift in shaft in physical rotational contact with said cam lift bearing surfaces;
wherein said cam lift is secured between said first and second contoured body members in both said closed position and an open position.

18. The system of claim 17, wherein said first selective height and said second selective height are sized to correspond to the size of an individual's disc space.

19. The system of claim 17, wherein said first selective height and said second selective height are identical.

20. The system of claim 17, wherein said first selective height and said second selective height are different.

21. The system of claim 17, wherein said plurality of contoured body members have heights ranging from 4 millimeters to 8 millimeters.

* * * * *